United States Patent
Sillerud et al.

(10) Patent No.: US 9,958,516 B2
(45) Date of Patent: *May 1, 2018

(54) BIOLOGICAL DETECTOR AND METHOD

(71) Applicants: STC.UNM, Albuquerque, NM (US); ABQMR, Inc., Albuquerque, NM (US); Sandia Corporation, Albuquerque, NM (US)

(72) Inventors: Laurel Sillerud, Albuquerque, NM (US); Todd M. Alam, Cedar Crest, NM (US); Andrew F. McDowell, Albuquerque, NM (US)

(73) Assignees: ABQMR, Inc., Albuquerque, NM (US); Sandia Corporation, Albuquerque, NM (US); STC.UNM, Albuquerque, NM (US)

( * ) Notice: Subject to any disclaimer, the term of this patent is extended or adjusted under 35 U.S.C. 154(b) by 1043 days.

This patent is subject to a terminal disclaimer.

(21) Appl. No.: 14/226,572

(22) Filed: Mar. 26, 2014

(65) Prior Publication Data

US 2014/0295486 A1 Oct. 2, 2014

Related U.S. Application Data

(63) Continuation of application No. 13/776,580, filed on Feb. 25, 2013, now Pat. No. 8,698,494, which is a
(Continued)

(51) Int. Cl.
*G01R 33/32* (2006.01)
*G01R 33/30* (2006.01)
(Continued)

(52) U.S. Cl.
CPC .............. *G01R 33/32* (2013.01); *B82Y 15/00* (2013.01); *G01N 24/08* (2013.01);
(Continued)

(58) Field of Classification Search
CPC .............................. G01R 33/32; G01R 33/302; G01R 33/34007; G01R 33/34046; G01R 33/341;
(Continued)

(56) References Cited

U.S. PATENT DOCUMENTS 4,901,018 A 2/1990 Lew
5,136,095 A 8/1992 Tarnowski et al.
(Continued)

FOREIGN PATENT DOCUMENTS

CA 2342047 9/2001
EP 1304581 A2 4/2003
(Continued)

OTHER PUBLICATIONS

"U.S. Appl. No. 13/717,412, Preliminary Amendment filed Dec. 17, 2012", 3 pgs.
(Continued)

*Primary Examiner* — Rodney Bonnette
(74) *Attorney, Agent, or Firm* — Schwegman Lundberg & Woessner, P.A.

(57) ABSTRACT

A biological detector includes a conduit for receiving a fluid containing one or more magnetic nanoparticle-labeled, biological objects to be detected and one or more permanent magnets or electromagnet for establishing a low magnetic field in which the conduit is disposed. A microcoil is disposed proximate the conduit for energization at a frequency that permits detection by NMR spectroscopy of whether the one or more magnetically-labeled biological objects is/are present in the fluid.

10 Claims, 9 Drawing Sheets

Related U.S. Application Data continuation of application No. 12/720,499, filed on Mar. 9, 2010, now Pat. No. 8,384,381, which is a continuation of application No. 11/894,597, filed on Aug. 21, 2007, now Pat. No. 8,339,135.

(60) Provisional application No. 60/839,006, filed on Aug. 21, 2006.

(51) Int. Cl.
| | |
|---|---|
| G01R 33/34 | (2006.01) |
| G01R 33/341 | (2006.01) |
| G01R 33/465 | (2006.01) |
| G01N 24/08 | (2006.01) |
| G01N 33/543 | (2006.01) |
| G01N 33/553 | (2006.01) |
| B82Y 15/00 | (2011.01) |
| G01R 33/28 | (2006.01) |
| G01R 33/56 | (2006.01) |

(52) U.S. Cl.
CPC ..... *G01N 33/54326* (2013.01); *G01N 33/553* (2013.01); *G01R 33/302* (2013.01); *G01R 33/341* (2013.01); *G01R 33/34007* (2013.01); *G01R 33/34046* (2013.01); *G01R 33/465* (2013.01); *G01R 33/281* (2013.01); *G01R 33/34092* (2013.01); *G01R 33/5601* (2013.01)

(58) Field of Classification Search
CPC ............... G01R 33/465; G01R 33/281; G01R 33/34092; G01R 33/5601; G01N 24/08; G01N 33/54326; G01N 33/553; B82Y 15/00
See application file for complete search history.

(56) References Cited

U.S. PATENT DOCUMENTS

| | | | |
|---|---|---|---|
| 5,164,297 A | 11/1992 | Josephson et al. | |
| 5,254,460 A | 10/1993 | Josephson et al. | |
| 5,338,687 A | 8/1994 | Lee et al. | |
| 5,654,636 A | 8/1997 | Sweedler | |
| 5,677,133 A | 10/1997 | Oberhardt | |
| 5,684,401 A | 11/1997 | Peck et al. | |
| 5,768,089 A | 6/1998 | Finnigan | |
| 5,773,307 A | 6/1998 | Colin et al. | |
| 5,925,573 A | 7/1999 | Colin et al. | |
| 6,097,188 A | 8/2000 | Sweedler et al. | |
| 6,194,900 B1 | 2/2001 | Freeman et al. | |
| 6,236,205 B1 | 5/2001 | Ludeke et al. | |
| 6,242,915 B1 | 6/2001 | Hurd | |
| 6,307,372 B1 | 10/2001 | Sugerman et al. | |
| 6,326,787 B1 | 12/2001 | Cowgill | |
| 6,361,944 B1 | 3/2002 | Mirkin et al. | |
| 6,397,094 B1 | 5/2002 | Ludeke et al. | |
| 6,456,072 B1 | 9/2002 | Webb et al. | |
| 6,487,437 B1 | 11/2002 | Viswanathan et al. | |
| 6,512,941 B1 | 1/2003 | Weiss et al. | |
| 6,587,706 B1 | 7/2003 | Viswanathan | |
| 6,594,517 B1 | 7/2003 | Nevo | |
| 6,696,838 B2 | 2/2004 | Raftery | |
| 6,699,669 B2 | 3/2004 | Vellinger et al. | |
| 6,788,061 B1 | 9/2004 | Sweedler et al. | |
| 6,822,454 B2 | 11/2004 | Peck et al. | |
| 6,845,262 B2 | 1/2005 | Albert et al. | |
| 6,958,609 B2 | 10/2005 | Raftery | |
| 7,096,057 B2 | 8/2006 | Hockett et al. | |
| 7,141,978 B2 | 11/2006 | Peck et al. | |
| 7,200,430 B2 | 4/2007 | Thomas et al. | |
| 7,202,667 B2 | 4/2007 | Barbic | |
| 7,271,592 B1 | 9/2007 | Gerald, II et al. | |
| 7,274,191 B2 | 9/2007 | Park et al. | |
| 7,345,479 B2 | 3/2008 | Park et al. | |
| 7,403,008 B2 | 7/2008 | Blank et al. | |
| 7,405,567 B2 | 7/2008 | McDowell | |
| 7,564,245 B2 | 7/2009 | Lee | |
| 8,102,176 B2 | 1/2012 | Lee | |
| 8,115,488 B2* | 2/2012 | McDowell | G01R 33/34 324/322 |
| 8,143,896 B2 | 3/2012 | Mcdowell et al. | |
| 8,334,693 B2 | 12/2012 | Lee et al. | |
| 8,339,135 B2 | 12/2012 | Sillerud et al. | |
| 8,384,381 B2 | 2/2013 | Sillerud et al. | |
| 8,698,494 B2 | 4/2014 | Sillerud et al. | |
| 8,710,836 B2* | 4/2014 | Adolphi | G01N 24/08 324/303 |
| 9,194,921 B2* | 11/2015 | Sillerud | B82Y 15/00 |
| 2002/0130661 A1 | 9/2002 | Raftery et al. | |
| 2002/0155599 A1 | 10/2002 | Vellinger et al. | |
| 2003/0088181 A1 | 5/2003 | Gleich | |
| 2003/0092029 A1 | 5/2003 | Josephson et al. | |
| 2003/0222648 A1 | 12/2003 | Fan | |
| 2004/0018611 A1 | 1/2004 | Ward | |
| 2005/0245814 A1 | 11/2005 | Anderson et al. | |
| 2007/0090836 A1 | 4/2007 | Xiang | |
| 2007/0116602 A1 | 5/2007 | Lee | |
| 2007/0152669 A1 | 7/2007 | Park et al. | |
| 2007/0152670 A1 | 7/2007 | Park et al. | |
| 2008/0204022 A1 | 8/2008 | Sillerud et al. | |
| 2008/0272788 A1 | 11/2008 | McDowell | |
| 2008/0315875 A1 | 12/2008 | Sillerud | |
| 2009/0134869 A1 | 5/2009 | Lee | |
| 2009/0139908 A1 | 6/2009 | Zhou et al. | |
| 2009/0146658 A1 | 6/2009 | McDowell et al. | |
| 2009/0256572 A1 | 10/2009 | McDowell | |
| 2010/0072994 A1 | 3/2010 | Lee et al. | |
| 2010/0207631 A1 | 8/2010 | Mcdowell | |
| 2010/0219824 A1 | 9/2010 | Sillerud et al. | |
| 2011/0018538 A1 | 1/2011 | Lee | |
| 2011/0091987 A1 | 4/2011 | Weissleder et al. | |
| 2012/0100546 A1 | 4/2012 | Lowery, Jr. et al. | |
| 2012/0112744 A1 | 5/2012 | Mcdowell et al. | |
| 2013/0127464 A1 | 5/2013 | Sillerud et al. | |
| 2013/0169276 A1 | 7/2013 | Sillerud et al. | |

FOREIGN PATENT DOCUMENTS

| | | |
|---|---|---|
| WO | WO-0173460 A1 | 10/2001 |
| WO | WO-02098364 A2 | 12/2002 |
| WO | WO-2002098364 A2 | 12/2002 |
| WO | WO-2005026762 A1 | 3/2005 |
| WO | WO-2008119054 A1 | 10/2008 |
| WO | WO-2008137721 A2 | 11/2008 |
| WO | WO-2009055587 A1 | 4/2009 |

OTHER PUBLICATIONS

"U.S. Appl. No. 13/717,412, Response filed Jul. 23, 2014 to Final Office Action dated May 23, 2014", 7 pgs.

"International Application Serial No. PCT/US2008/058518, International Preliminary Report on Patentability dated Sep. 29, 2009", 12 pgs.

"International Application Serial No. PCT/US2008/062473, International Preliminary Report on Patentability dated Nov. 3, 2009", 3 pgs.

"International Application Serial No. PCT/US2008/080983, International Preliminary Report on Patentability dated Apr. 27, 2010", 11 pgs.

"International Application Serial No. PCT/US2009/067577, International Preliminary Report on Patentability dated Jun. 14, 2011", 9 pgs.

Fan, H., et al., "Self-Assembly of Ordered, Robust, Three-Dimensional Gold Nanocrystal/Silica Arrays", *Science* 304(5670), (Apr. 2004) 567-571.

Massin, C., et al., "Planar microcoil-based microfluidic NMR probes", *J. Magn. Reson.*, 164(2), (2003), 242-255.

Perez, J. M., et al., "Viral-Induced Self-Assembly of Magnetic Nanoparticles Allows the Detection of Viral Particles in Biological Media", *J. Am. Chem. Soc.*, 125(34), (2003) 10192-10193.

(56) References Cited

OTHER PUBLICATIONS

Williams, J. D., et al., "Microfabrication of an electromagnetic power relay using SU-8 based UV-LIGA technology", *Microsystem Technologies*, 10(10), (Dec. 2004), 699-705.
Zhao, X., et al., "A rapid bioassay for single bacterial cell quantitation using biconjugated nanoparticles", *Proc Natl Acad Sci USA.*, 101(42), (Oct. 19, 2004), 15027-15032.
"U.S. Appl. No. 13/717,412, Final Office Action dated May 23, 2014", 6 pgs.
Lacey, Michael E., et al., "High-Resolution NMR Spectroscopy of Sample Volumes from 1 nL to 10 µL", Chem Rev., 1999, 99 (10), pp. 3133-3152, Copyright American Chemical Society, (Sep. 16, 1999), 3133-3152.
"U.S. Appl. No. 13/717,412, Non Final Office Action dated Apr. 8, 2015", 5 pgs.
"U.S. Appl. No. 13/717,412, Notice of Allowance dated Jul. 23, 2015", 6 pgs.
"U.S. Appl. No. 13/717,412, Response filed Jun. 30, 2015 to Non Final Office Action dated Jun. 30, 2015", 5 pgs.
U.S. Appl. No. 60/981,948, filed Oct. 23, 2007, McDowell, et al.
U.S. Appl. No. 61/099,975, filed Sep. 25, 2008, McDowell, et al.
"U.S. Appl. No. 11/894,597, Non Final Office Action dated Nov. 9, 2011", 9 pgs.
"U.S. Appl. No. 11/894,597, Non Final Office Actio dated Mar. 5, 2009", 6 pgs.
"U.S. Appl. No. 11/894,597, Notice of Allowance dated Aug. 21, 2012", 9 pgs.
"U.S. Appl. No. 11/894,597, Notice of Allowance dated Dec. 3, 2009", 10 pgs.
"U.S. Appl. No. 11/894,597, Response filed Apr. 9, 2012 to Non-Final Office Action dated Nov. 9, 2011", 16 pgs.
"U.S. Appl. No. 11/894,597, Response filed Sep. 4, 2009 to Non Final Office Action dated Mar. 5, 2009", 14 pgs.
"U.S. Appl. No. 12/075,234, Office Action dated Apr. 27, 2009", 7 pgs.
"U.S. Appl. No. 12/114,538, Non-Final Office Action and Examiner's Search Strategy dated Jul. 29, 2010", 103 pgs.
"U.S. Appl. No. 12/720,499, Notice of Allowance dated Oct. 17, 2012", 9 pgs.
"U.S. Appl. No. 12/720,499, Preliminary Amendment filed Mar. 9, 2010", 8 pgs.
"U.S. Appl. No. 12/720,541, Pending Claim Set", 11 pgs, Oct. 24, 2011.
"U.S. Appl. No. 13/717,412, Response filed Aug. 21, 2013 Non Final Office Action dated May 21, 2013", 8 pgs.
"U.S. Appl. No. 13/717,412, Non Final Office Action dated May 21, 2013", 17 pgs.
"U.S. Appl. No. 13/717,412, Preliminary Amendment filed Feb. 22, 2013", 5 pgs.
"U.S. Appl. No. 13/776,580, Response filed Sep. 17, 2013 to Non Final Office Action dated Jun. 14, 2013", 8 pgs.
"U.S. Appl. No. 13/776,580, Non Final Office Action dated Jun. 14, 2013", 6 pgs.
"U.S. Appl. No. 13/776,580, Notice of Allowance dated Nov. 29, 2013", 8 pgs.
"U.S. Appl. No. 13/776,580, Preliminary Amendment filed Feb. 25, 2013", 6 pgs.
"Detecting Labeled Entities Using Microcoil MRI", U.S. Appl. No. 60/920,165, filed Mar. 27, 2007, 16 pgs.
"International Application Serial No. PCT/US2008/058518, claims filed Mar. 27, 2008", (Mar. 27, 2008), 8 pgs.
"International Application Serial No. PCT/US2008/058518, Notification of Transmittal of the International Search Report and the Written Opinion of the International Search Authority dated Jul. 7, 2008", 21 pgs.
"International Application Serial No. PCT/US2008/062473, claims filed May 2, 2008", (May 2, 2008), 4 pgs.
"International Application Serial No. PCT/US2008/062473, Notification of Transmittal of the International Search Report and the Written Opinion of the International Search Authority dated Oct. 29, 2008", 23 pgs.
"International Application Serial No. PCT/US2008/080983, claims filed Oct. 23, 2008", (Oct. 23, 2008), 8 pgs.
"International Application Serial No. PCT/US2008/080983, International Search Report and Written Opinion dated Mar. 3, 2009", 20 pgs.
"International Application Serial No. PCT/US2009/067577, claims filed Dec. 10, 2009", (Dec. 10, 2009), 14 pgs.
"International Application Serial No. PCT/US2009/067577, International Search Report and Written Opinion dated Feb. 2, 2010", 13 pgs.
"Poster", 8th ICMRM, Utsunomiya, Japan, Aug. 22-26, 2005, (Aug. 2005), 15 pgs.
Abragam, "The Principles of Nuclear Magnetism", Clarendon Press, Oxford, (1961), 71-83.
Adams, David, et al., "Bioagent Detection Using Miniaturize NMR and Nanoparticle Amplification", U.S. Appl. No. 60/839,006, filed Aug. 21, 2006, 15 pgs.
Adolphi, Natalie, "Improved Microcoil NMR Devices", U.S. Appl. No. 61/121,416, filed Dec. 10, 2008, 5 pgs.
Adolphi, Natalie, "Nuclear Magnetic Resonance Apparatus Method and Associated Technology", U.S. Appl. No. 12/635,583, filed Dec. 10, 2009, 66 pgs.
Alam, Todd, et al., "Bioagent Detection Using Minaturized NMR and Nanoparticle Amplification Technical Advance Description: Bioagent Detection Using Minaturized NMR and Nanoparticle Amplification", Sandia Technical Advance Description SD7956, (Mar. 8, 2005), 4 pgs.
Armenean, et al., "NMR Radiofrequency Microcoil Design: Electromagnetic Simulation Usefulness", Compes Rendus—Biologies, Elsevier, Paris, vol. 325, No. 4, (Apr. 1, 2002), 457-463.
Armenean, et al., "Solenoidal and Planar Microcoils for NMR Spectroscopy", Proceedings of the 25th Annual International Conference of the IEEE Engineering in Medicine and Biology Society, Cancun, Mexico, (Sep. 17, 2003), 3045-3048.
Fukushima, et al., "Experimental Pulse NMR—A Nuts and Bolts Approach", Addison-Wesley Pub. Co., MA, (1981), 311, 342, and 372.
Goloshevsky, et al., "Development of Low Field Nuclear Magnetic Resonance Microcoils", Review of Scientific Instruments, vol. 76, (2005), 024101-024101-6.
Henson, et al., "Introduction to Magnetic Resonance Microscopy", Department of Cell Biology and Anatomy at The University of North Carolina at Chapel Hill, [Online]. Retrieved from the Internet: <http://web.archive.org/web/20040824113019/http://cbaweb2.med.unc.edu/henson_mrm/pages/mrmfaq.html>, (2004), 1-9.
Hoult, et al., "The Signal-to-Noise Ratio of the Nuclear Magnetic Resonance Experiment", Journal of Magnetic Resonances, vol. 24, (1976), 71-85.
Kaittanis, et al., "One-Step, Nanoparticle-Mediated Bacterial Detection with Magnetic Relaxation", Nano Letters, vol. 7, No. 2, (2007), 381-383.
Lee, et al., "Chip-NMR Biosensor for Detection and Molecular Analysis of Cells", Nature Medicine, vol. 14, No. 8, (Aug. 2008), 869-874.
Magin, et al., "Miniature Magnetic Resonance Machines", IEEE Spectrum, IEEE Inc. New York, vol. 34, No. 10, (Oct. 1, 1997), 51-61.
Massin, et al., "Planar Microcoil-Based Magnetic Resonance Imaging of Cells", Transducers '03, The 13th International Conference on Solid State Sensors, Actuators and Microsystems, Boston, (Jun. 8-12, 2003), 967-970.
McDowell, et al., "Low-Field Micro-Coil Probe Development for Portable NMR", 8th ICMRM Utsunomiya, Japan (pp. 2-14 are a magnification of p. 1), (Aug. 22-26, 2005), 14 pgs.
McDowell, Andrew F., et al., "Low-field micro-coil probe development for portable NMR", 8th ICMRM, The Heidelberg Conference, Mibu, Japan, Conference Program Abstract, Aug. 22-26, 2005, (Aug. 22, 2005), 1 pg.

(56) References Cited

OTHER PUBLICATIONS

McDowell, Andrew, et al., "Operating Nano Liter Scale NMR Microcoils in a 1 Tesla Field", U.S. Appl. No. 60/927,456, filed May 3, 2007, 25 pgs.

McDowell, Andrew F., et al., "Operating nanoliter scale NMR microcoils in a 1 tesla field", Journal of Magnetic Resonance 188 (2007) 74-82, (Jun. 30, 2007), 74-82.

McDowell, Andrew, "Tuning Low-Inductance Coils at Low Frequencies", U.S. Appl. No. 12/720,541, filed Mar. 9, 2010, 39 pgs.

Minard, et al., "Solenoidal Microcoil Design. Part 1: Optimizing RF Homogeneity and Coil Dimensions", Concepts in Magn. Reson., vol. 13, (2001), 128-142.

Moresi, et al., "Miniature Permanent Magnet for Table-Top NMR", Concept Magn. Reson., vol. 19B, (2003), 35-43.

Peck, et al., "Design and Analysis of Microcoils for NMR Microscopy", Journal of Magnetic Resonance, Series B, vol. 108, (1995), 114-124.

Peck, et al., "RF Microcoils Patterned Using Microlithographic Techniques for Use as Microsensors in NMR", Engineering in Medicine and Biology Society, Proceedings of the 15th Annual International Conference of the IEEE, (Oct. 28-31, 1993), 174-175.

Seeber, et al., "Design and Testing of High Sensitivity Microreceiver Coil Apparatus for Nuclear Magnetic Resonance and Imaging", Review of Scientific Instruments, vol. 72, No. 4, (Apr. 2001), 2171-2179.

Seeber, D. A, et al., "Triaxial Magnetic Field Gradient System Microcoil Magnetic Resonance Imaging", Review of Scientific Instruments, 71(11), (Nov. 2000), 4263-4272.

Sillerud, Laurel O., "A Portable, Miniature, NMR Detection System Using Nanoparticle Signal Amplification for Biowarfare Agents", (2007), 4 pgs.

Sillerud, Laurel, "Biological Detector and Method", U.S. Appl. No. 12/720,499, filed Mar. 9, 2010, 48 pgs.

Sillerud, Laurel O., et al., "H NMR Detection of superparamagnetic nanoparticles at 1 T using a microcoil and novel tuning circuit", Journal of Magnetic Resonance 181 (2006) 181-190, (2006), 181-190.

Sillerud, Laurel, "Protest Under 37 CFR 1.291", U.S. Appl. No. 12/720,499, filed Apr. 26, 2010, (Apr. 26, 2010), 77 pgs.

Sillerud, Laurel O., et al., "Research Plan", (2007), 33 pgs.

Sorli, et al., "Micro-Spectrometer for NMR: Analysis of Small Quantities in vitro", Measurement Science and Technology, vol. 15, (2004), 877-880.

Subramanian, et al., "RF Microcoil Design for Practical NMR of Mass-Limited Samples", Journal of Magnetic Resonance, Academic Press, Orlando, Florida, vol. 133, No. 1, (Jul. 1, 1998), 227-231.

Taktak, et al., "Multiparameter Magnetic Relaxation Switch Assays", Analytical Chemistry, vol. 79, No. 23, (Dec. 1, 2007), 8863-8869.

Van Bentum, et al., "Towards Nuclear Magnetic Resonance u-Spectroscopy and u-Imaging", Analyst, Royal Society of Chemistry, London, vol. 129, No. 9, (Jan. 1, 2004), 793-803.

Wu, Nian, et al., "H-NMR Spectroscopy on the Nanoliter Scale for Static and On-Line Measurements", Anal. Chem. 1994, 66, (1994), 3849-3857.

\* cited by examiner

BIOLOGICAL DETECTOR AND METHOD

This application is a continuation of U.S. patent application Ser. No. 13/776,580, filed Feb. 25, 2013, issued as U.S. Pat. No. 8,698,494, which is a continuation of U.S. patent application Ser. No. 12/720,499, filed Mar. 9, 2010, issued as U.S. Pat. No. 8,384,381, which is a continuation of U.S. patent application Ser. No. 11/894,597 filed Aug. 21, 2007, issued as U.S. Pat. No. 8,339,135, which claims the benefit of U.S. Provisional Application No. 60/839,006, filed Aug. 21, 2006, all of which are incorporated herein by reference in their entirety.

GOVERNMENT INTEREST STATEMENT

This invention was developed under Contract DE-AC04-94AL85000 between Sandia Corporation and the U.S. Department of Energy. The U.S. Government has certain rights in this invention.

FIELD OF THE INVENTION

The invention relates to a NMR-based biological detector and detection method that involves NMR detection of magnetic nanoparticle-labeled biological objects using a microcoil.

BACKGROUND OF THE INVENTION

Nuclear magnetic resonance (NMR) spectroscopy is widely used for the real-time identification of chemical compounds in solids, liquids, and gases because it can easily detect and characterize all components of mixtures without requiring separations. Unfortunately, standard high-resolution NMR spectroscopy is not useful for directly detecting dilute biological objects, such as tumor cells, bacteria, bacterial toxins, or viruses, in fluid samples. The weak signals from the analytes in the dilute species are lost against the much stronger background water signal. Even if the dynamic range challenge is met by suppressing the bulk water signal or concentrating the dilute species, the rapid transverse relaxation characteristics of macromolecular, viral, or cellular samples renders their direct detection by NMR difficult.

Recent developments involving superparamagnetic iron oxide nanoparticles (SPIONs) have, however, supplied the basis for new applications of NMR with high sensitivity and specificity for the detection and quantitation of dilute biological materials in fluids, such as cancer cells in blood or urine samples, or bacterial contaminants in food products or drinking water.

SPIONs are enjoying significant uses as biological contrast agents for NMR imaging in human clinical medicine. Furthermore, these nanoparticles can be coupled with biologically specific recognition ligands to target epitopes involved in diseases, like cancer. The her-2 protein, for example, is over-produced in many breast cancers and has been the subject of successful NMR imaging experiments where cells displaying this protein have been specifically imaged by means of SPIONs labeled with anti-her-2 antibodies. The image contrast effects due to SPIONs, which are typically embedded in larger beads, rely on the enhancement of the relaxation rates of water molecules surrounding the beads. The magnetic field gradient from a single, micron-sized magnetic bead has been shown to influence the relaxation time $T^*_2$ of the surrounding water within a voxel approximately 100 μm on a side (a volume of 1 nL), which is about 1000 times larger than that of a single cell. Thus, for a small biological object bound to a magnetic bead in water, the change in the NMR signal caused by the presence of the object is greatly amplified by the effect of the magnetic bead on the surrounding water.

In recent years, significant advances in the development and fabrication of microcoils (size<1 mm) for NMR have continued. Both planar surface microcoils and solenoidal microcoils have been developed. To enhance sensitivity for tiny samples, much of the work with microcoils has utilized the high fields produced by strong superconducting magnets.

SUMMARY OF THE INVENTION

The invention provides in an illustrative embodiment an NMR-based biological detector and detection method that involve detection of one or more magnetic nanoparticle-labeled biological objects in a fluid, such as water, contained in a fluid-receiving conduit using a microcoil and a magnetic field generator, such as one or more low field permanent magnets or electromagnets, to establish a relatively low magnetic field with energization of the microcoil at a frequency that permits detection by NMR of one or more biological objects present in the fluid.

In an illustrative embodiment of the present invention, the microcoil has an inner diameter of about 50 to about 550 microns, preferably about 75 to about 125 microns, and even more preferably about 100 microns. The microcoil can comprise a solenoid-shaped or a flat, planar shaped microcoil. The solenoid-shaped microcoil preferably comprises a metallic wire microcoil wound on a tubular microconduit to reduce cost of the detector. The fluid in the tubular conduit is disposed in a magnetic field of about 0.5 to about 1.5 T established by one or more permanent magnets or electromagnets. The microcoil on the conduit can be mounted on a ceramic chip substrate to provide a compact assembly. A microfluidic chip also can be used to this end.

The NMR-based detector can provide capability of performing routine relaxation time measurements and low-field spectroscopy for the detection of dilute concentrations of magnetic nanoparticle-labeled biological objects in fluids. Such biological objects include, but are not limited to, cancer cells in blood or urine samples, bacterial contaminants in food products or drinking water, and biological warfare agents in aqueous media.

The present invention is advantageous in a preferred embodiment in providing a microcoil together with one or more compact permanent magnets with benefits of reduced cost, maintenance, and space requirements of the NMR-based detector as well as portability thereof.

Other advantages of the invention will become apparent from the following detailed description taken with the following drawings.

DESCRIPTION OF THE DRAWINGS

FIG. 9A is data from water doped with GdDTPA with $T_1$ determined being 65±4 ms. FIG. 9B is data from de-ionized water with $T_1$ determined being 1.0±0.2 s. FIG. 9C is data from a 1:10 dilution of Dynabeads in de-ionized water with the relaxation time $T_1$ determined being 0.64±0.17 s.

DETAILED DESCRIPTION OF THE INVENTION

The invention provides an NMR-based biological detector and detection method for detection of one or more magnetic nanoparticle-labeled biological objects in a fluid, such as water. The fluid can be contained in a closed or open microconduit, such as a capillary tube or open-sided microchannel on or in a substrate (microfluidic chip), or other fluid sample holder. The fluid can be introduced to the conduit by injection using a fluid sample syringe for example, by capillary action using a capillary tube as the conduit, under pressure by a micropump for example, and/or any other technique and can be static in the conduit or can flow through the conduit during practice of the invention. The NMR-based detector includes a microcoil and a magnetic field generator, such as one or more low field permanent magnets or electromagnets, to establish a magnetic field of about 0.5 to about 1.5 T (Tesla) with energization of the microcoil at a frequency that permits detection by NMR of one or more labeled biological objects present in the fluid in the conduit. The NMR-based detector can provide capability of performing routine relaxation time measurements and low-field spectroscopy for the detection of dilute concentrations of magnetic nanoparticle-labeled biological objects in biological fluids such as blood, saliva, and serum as well as aqueous fluids such as drinking water and aqueous industrial waste or effluent streams or spills. Such biological objects include, but are not limited to, cancer cells in blood or urine samples, bacterial contaminants in food products or drinking water, and biological warfare agents in aqueous media.

Figure 1:
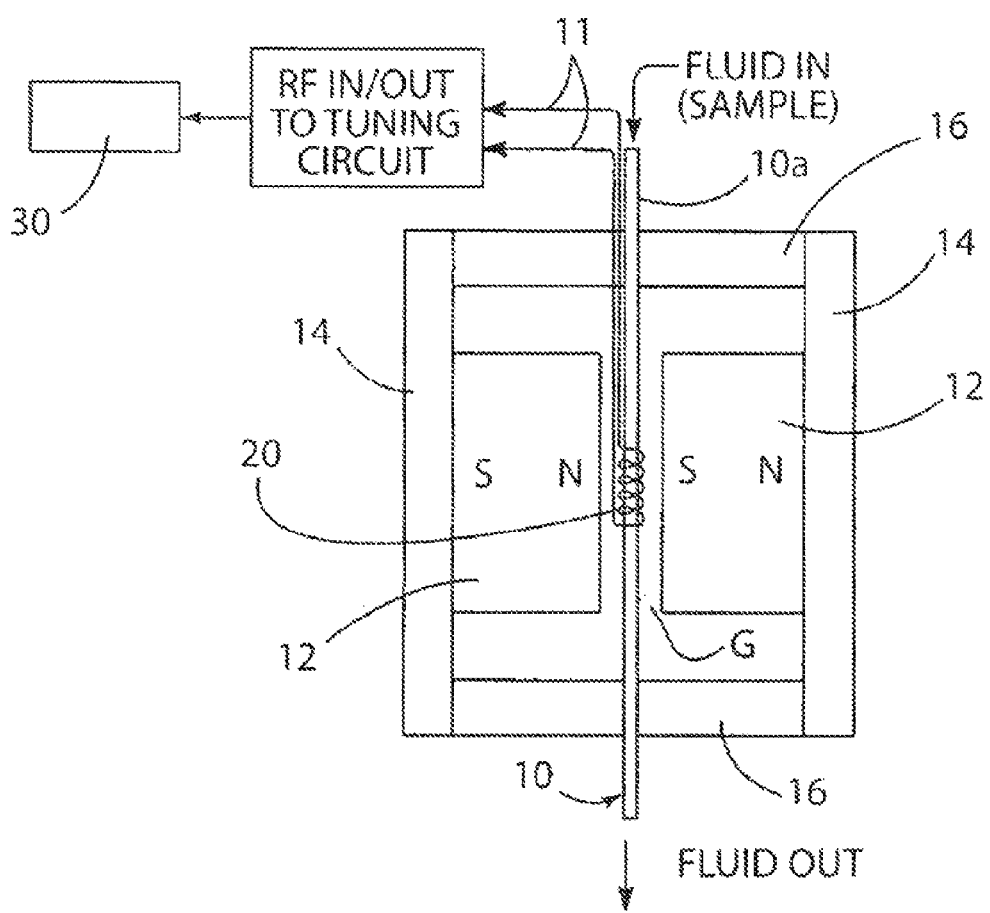
FIG. 1 is a schematic view of an NMR-based detector in accordance with an illustrative embodiment of the invention.

Referring to FIG. 1, an NMR-based detector pursuant to an illustrative embodiment of the present invention is schematically shown and includes a fluid-receiving conduit 10 in the form a capillary tube 10a that resides in a gap G between opposite polarity ends N, S of first and second permanent magnets 12 that provide a magnetic field of about 0.5 to about 1.5 T in the gap. The permanent magnets 12 are disposed on respective soft iron, steel, or other ferrous support members 14 by adhesive or any fastening technique. Soft iron flux-carrying members 16 are shown disposed between the support members 14 to complete the magnetic flux path therebetween of the magnet assembly.

The permanent magnets 12 can comprise cylindrical shaped commercially available SmCo, NdFeB or other low field permanent magnets that provide a magnetic field in the range of about 0.5 to about 1.5 T. For example, suitable SmCo and NdFeB permanent magnets are available from Neomax, Osaka, Japan. For purposes of illustration and not limitation, such permanent magnets can have a diameter of 2 inches and length of 2 inches and provide a gap of 0.05 inch width in which the conduit 10 is disposed. The permanent magnets can have any shape in practice of the invention. One or more permanent magnets, or a single C-shaped or similar shaped permanent magnet having integral opposite polarity ends at a gap can be used in practice of the invention.

Use of one or more low field compact permanent magnets with the microcoil 20 to be described below provides benefits of reduced cost, maintenance, and space requirements for the NMR-based detector as well as imparts portability to the detector.

However, the present invention also can be practiced using one or more electromagnets to provide a low magnetic field of about 0.5 to 1.5 T in lieu of the one or more permanent magnets described above. An electromagnet that can be used can comprise a high quality solenoid, or an iron-core magnet with polished pole faces.

Referring to FIG. 1, a microcoil 20 is shown disposed about the outer periphery of the conduit 10. In particular, the microcoil 20 is shown disposed about and on the periphery of the capillary tube 10a in the gap G. The microcoil 10 is connected by electrical leads 11 to a tuning circuit 30 described below in the Example to energize the microcoil at a frequency that permits detection by NMR of one or more magnetic nanoparticle-labeled biological objects present in the fluid. The microcoil 20 can be energized to provide the capability of performing routine relaxation time measurements and low-field spectroscopy for the detection of dilute concentrations of one or more magnetic nanoparticle-labeled biological objects in the fluid in the conduit 10.

The solenoid-shaped microcoil 20 illustrated in FIG. 1 can have an inner diameter of about 50 to about 550 microns, preferably about 75 to about 125 microns, and even more preferably about 100 microns determined by the outer diameter of the capillary tube 10a when the microcoil is fabricated directly on the tube. For example, the solenoid-shaped microcoil 20 illustrated in FIG. 1 can be formed by depositing one or more metallic layers on the cylindrical capillary and micromachining the layers to form a solenoid-shaped microcoil as described in the Example below. Alternately, the solenoid-shaped microcoil 20 can be formed by winding a metallic wire (e.g. a 50 gauge copper wire) directly on a tubular conduit to reduce cost of the detector. Winding of the metallic wire on the capillary tube is achieved by e.g., using small lathe to rotate the tube.

As described below in the Example, the conduit 10, the permanent magnets 12 (or one or more electromagnets if used), and the microcoil 20 can be disposed or mounted on a ceramic chip substrate C (see FIG. 4) to provide a compact assembly for use in a portable NMR-based detector.

The invention envisions detecting dilute concentrations of one or more specific magnetic nanoparticle-labeled biological objects in the fluid by performing routine relaxation time measurements and low-field spectroscopy. For example, for purposes of illustration and not limitation, such biological objects include, but are not limited to, cancer cells in blood or urine fluid samples, bacterial contaminants in fluid food products or drinking water, biological contaminants in waste water or spills, and biological warfare agents in aqueous fluid media.

The biological objects of the fluid are labeled using specific biological ligands (e.g. antibodies), which are carried on super-paramagnetic or other magnetic nanoparticles detectable by NMR. The nanoparticles can include, but are not limited to, superpara-magnetic iron oxide nanoparticles (SPIONs), or nanoparticles made out of cobalt, manganese, nickel, or other small paramagnetic materials. The surfaces of the nanoparticles typically are partially or fully covered or encapsulated by the specific biological ligand (e.g. antibody) to this end, although other particle surface chemistry may be employed in practice of the invention to provide desired NMR-detectable bioconjugations with the biological objects to be detected.

The recognition of the biological objects by the magnetic-labeled ligands (e.g. antibodies) results in a perturbation of the magnetic relaxation times ($T_1$, $T_2$, $T_2^*$) and properties of the fluid (water) molecules in the NMR fluid sample to amplify the recognition event to an extent to permit NMR detection of dilute concentrations of the labeled biological objects. The magnetic perturbations emanating from the presence of super-paramagnetic nanoparticles are so strong that only a few, possibly one, biological object may be needed to provide a detectable change in the NMR signal. The recognition of the biological objects by the magnetic-labeled ligands (e.g. antibodies) may or may not result in nano-self-assembly of the labeled biological objects. That is, the present invention does not require that self-assembly of the labeled biological objects occur.

The following EXAMPLE is offered to further illustrate the invention without limiting the invention in any way:

EXAMPLE

This Example involves an NMR-based detector having a 550 µm inner diameter, solenoidal microcoil deposited and micromachined on a capillary tube. Superparamagnetic iron oxide nanoparticles (SPIONs) are shown to measurably change the nuclear magnetic resonance (NMR) relaxation properties of nearby protons in aqueous solution.

Figure 2:
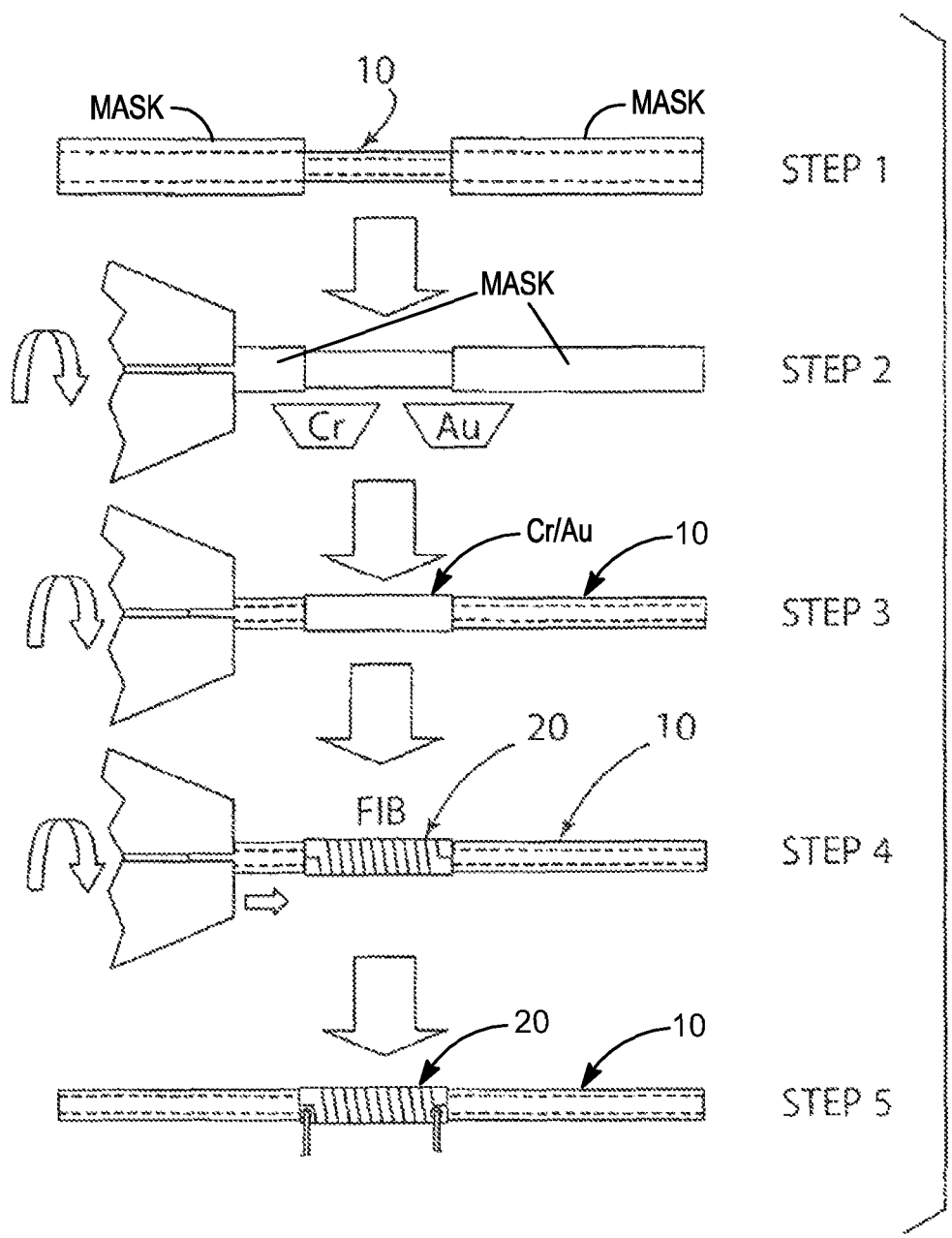
FIG. 2 is a flow chart showing a particular illustrative sequence of steps for fabrication of a microcoil and connection to electrical leads.

Microcoils were fabricated onto quartz tubes each having a length of 2.5 cm and a 550 µm outer diameter and 400 µm inner diameter using the procedure depicted in FIG. 2. The quartz tubes are commercially available from Vitrocom, Mountain Lakes, N.J. Each tube was cleaned using hydrogen peroxide followed by acetone and isopropyl alcohol. After wet chemical treatment, the tubes were masked on each end (step 1, FIG. 2), and the 6.2 mm unmasked center targeted for metal deposition was etched for 15 minutes using a 100 W $O_2$/Ar plasma. The central region length was chosen based on the coil design with two 2 mm-long cuffs on either end. The masked tubes were mounted into conventional individual pin vice fixtures for metal deposition. A stage having eight individual rotation stations contained within a high-vacuum thin film deposition chamber allowed for simultaneous coating of multiple tubes at a constant working distance of 35 cm. Electron beam evaporation was used to deposit a thin Cr layer (200 Å) followed by a relatively thick Au layer (5 µm) around the circumference of the tubes (step 2). Deposition rates were chosen to minimize the stress in the Cr and Au layers. After removal of the quartz tubes from the deposition system, the masks were removed using acetone (step 3), and the tubes were re-mounted into conventional pin vice fixtures for rotation within the focused ion beam (FIB) system (step 4).

Thirty keV Ga ions emitted from a liquid metal ion source were used to remove (micromachine) the Au/Cr layer in order to define the coil and the neighboring cuffs 20c. The ion beam was focused to approximately 0.5 µm width using a dual-lens Magnum ion column from FEI Co., Hillsboro, Oreg., and steered across areas outlined by the operator until all the metal was removed from targeted regions (step 4). Rates of metal removal were on the order of 10 µm$^3$/s when using a 20 nA Ga beam. Minimal heat and force accompany FIB bombardment. The secondary electron intensity was monitored during ion bombardment to ensure complete removal of metal and slight penetration into the quartz.

Figure 3:
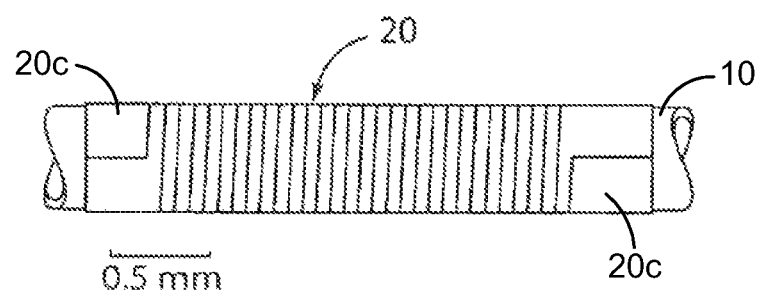
FIG. 3 is a perspective view of a microcoil made pursuant to FIG. 2 and used in testing described below in the Example. A 0.5 mm scale bar also is shown.

An example microcoil is shown in FIG. 3 (which includes a 0.5 mm scale bar) with areas removed by the FIB appearing as black lines. As indicated in FIG. 2, step 4, the sample was rotated by an in-vacuum, single-axis rotary stage and translated by a high precision x-y stage along the tube axis in order to define a helix. The motion-control system, consisting of an ultra-high vacuum compatible stepper motor (controlled by a Princeton Research Instruments stepper motor unit) and a reduction gear assembly, could orient a sample with 0.25° precision. This FIB method possibly may be used to fabricate microcoils onto much smaller tubes having approximately 50 µm outer diameter.

The finished metallic coil used in this Example (FIG. 3-4) had 28 turns over a length of 2.1 mm. The coil conductors were 65 µm wide with a gap between turns of 10 µm. The sample detection volume within the NMR microcoil was 264 nL. The filling factor was $(400/550)^2 = 53\%$. On the 2-mm long metallic cuffs of the coil, the FIB removed a 10-µm wide line parallel to the tube axis in order to interrupt conduction. The secondary electron detector within the FIB system also enabled registration of the coil turns. The direct current resistance (measured using a Fluke model 179 resistance measurement unit) of the micromachined coil was found to be 5.42 Ohms. The resistivity of the evaporated Au is 2.898 pOhm-cm (measured on a flat substrate), somewhat higher than bulk Au. Using this value and the geometry of the microcoil, a DC resistance of 4.3 Ohms was calculated. This differs from the measured resistance, perhaps due to contact resistance in the silver epoxy used to attach the coil to the circuit board. The microcoil inductance was calculated to be 93 nH.

Figure 4:
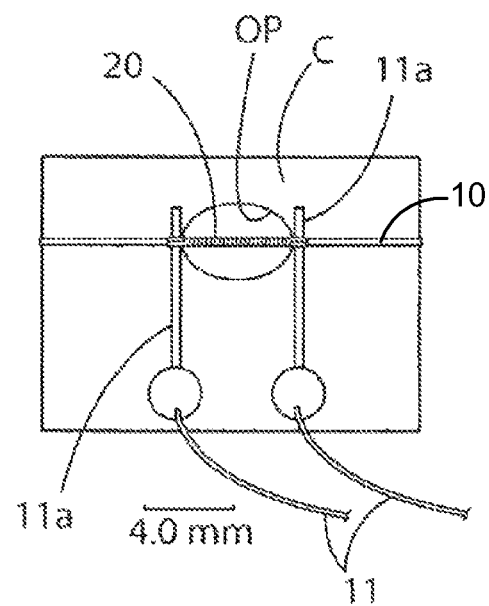
FIG. 4 is a plan view of the microcoil on the fluid sample conduit mounted on a ceramic chip substrate with electrical connections partially shown. A 4.0 mm scale bar also is shown.

The microcoil/capillary tube were packaged on a ceramic chip substrate C comprising DuPont™ Green Tape™ Low Temperature Co-Fired Ceramic (LTCC) material available from DuPont Microcircuit Materials, Research Triangle Park, N.C. The chip substrate had dimensions of 20 mm by 60 mm. The chip substrate had been previously plated with alloyed gold (Au—Pt) co-firable material (DuPont 5739) solder leads 11a as shown in FIG. 4 which are connected to leads 11. The microcoil was secured to the alloyed gold leads by means of silver-containing epoxy (FIG. 4 and schematically shown as step 5, FIG. 2), the alloyed gold leads supporting the microcoil on the chip substrate above an opening OP (FIG. 4) in the substrate. The opening assured that the microcoil did not contact the supporting platform and prevented distortion or damage to the very thin metal layer. Mounting of the microcoil on the ceramic chip substrate in this way allowed manipulation of the microcoil and attachment of the capillary tube on the substrate without damaging the coil.

$^1$H NMR measurements, at a resonant frequency of 44.2 MHz, were performed using a MRTechnology console (Tsukuba City, 300-2642 Japan), and a 1.04 T (Tesla) NEOMAX permanent magnet assembly comprising a NdFeB permanent magnet assembly providing a 2 inch gap. The microcoil on the chip substrate was inserted in the gap between the magnet pole faces with the chip substrate supported in the gap by plastic spacers for the NMR measurement. A smaller 1 Tesla permanent magnet suitable for use in a portable microcoil NMR device can be fabricated.

The transmitter pulses were output directly from the console, without a conventional radiofrequency power amplifier, because only 0.25 mW of power was required to produce a $B_1$ field of 0.3 G (vide infra). Ethanol (100%) was purchased from AAPER (Shelbyville, Ky.). Spin-lattice $^1$H $T_1$ values were obtained, using a standard inversion-recovery sequence, from a Gd-DTPA-containing water sample (Gd-DTPA is gadolinium-diethylene-triamine-pentaacetate), from a sample of magnetic beads in water, and from a sample of de-ionized water.

Magnetic beads (Dynabeads; MyOne Streptavidin) were purchased from Dynal Inc. Each magnetic bead consists of thousands of 8-nm diameter superparamagnetic iron oxide particles, uniformly dispersed in a polystyrene matrix, and coated with a thin layer of polymer and a monolayer of streptavidin which served as a bonding agent onto which biotinylated antibodies could be attached. The beads are 26% Fe by weight (about 10% Fe by volume) with an average diameter of 1.05±0.10 µm. The stock solution has a stated bead concentration of between $7 \times 10^3$ and $1.2 \times 10^4$ beads per nL (equivalent to about 2.6 mg Fe/ml). NMR samples were prepared by diluting the same batch of stock solution with de-ionized water by factors of 10, 100, and 1000 to produce nominal concentrations of 1000, 100, and 10 beads per nL introduced to the detector tube by supply syringe. The relaxation time $T^*_2$ was determined by collecting a single free-induction decay (FID) and fitting the resulting spectrum with a Lorentzian, unless noted otherwise. The relative shift of the NMR frequency of water caused by the magnetic-labeled beads was determined by measuring the resonance frequency of each solution in a 5 mm NMR tube in a conventional coil relative to a separate tube of deionized water. To avoid errors due to field drift of the permanent magnet, each frequency shift measurement was performed by switching several times between the bead solution and a deionized water sample during a period when the frequency drift was confirmed to be less than 1 Hz/min.

The 93 nH inductance of the 550-µm outer diameter microcoil described above could reach resonance at 44.2 MHz with a variable capacitor of reasonable size. However, since use of much smaller microcoils at coil outer diameters nearer the 50 µm outer diameter are envisioned, described below are tuning circuits for tuning such smaller microcoils to resonance at the 44.2 MHz resonant frequency or less to detect water with a spectral resolution of 2.5 Hz in a 1.04 Tesla permanent magnet.

Such a tuning circuit involves an auxiliary tank circuit with conventional scale capacitors and to connect the microcoil to it. The key parameter of the microcoil described above that guided the design of this tuning circuit was its very high coil resistance. Optimization of a tuned circuit's SNR (where SNR is the signal to noise ratio) is a compromise between maximizing coil efficiency, in terms of the magnetic field produced per unit current in the sample coil, while minimizing the resistive noise. The dominant noise source for the very thin, ribbon-wire shaped microcoils used in this Example was its large coil resistance. Therefore, the introduction of the additional inductor did not degrade performance, because this extra inductance did not contribute to the resistive losses.

Figure 5A:
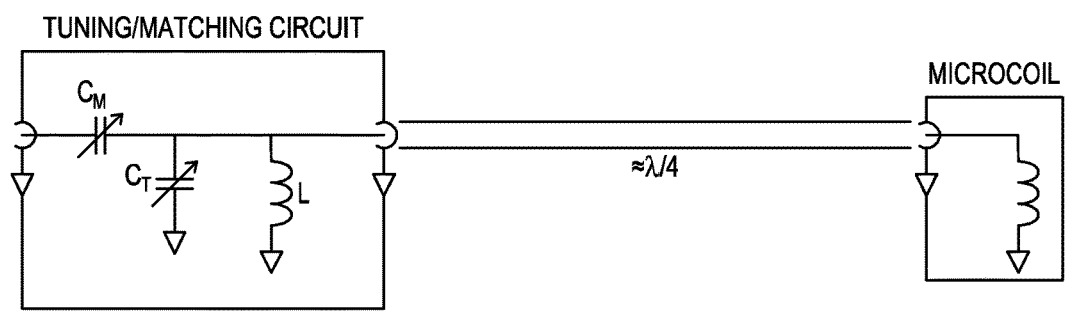
FIGS. 5A and 5B illustrate different probe circuits for tuning the low-inductance microcoil at low frequency.
Figure 5B:
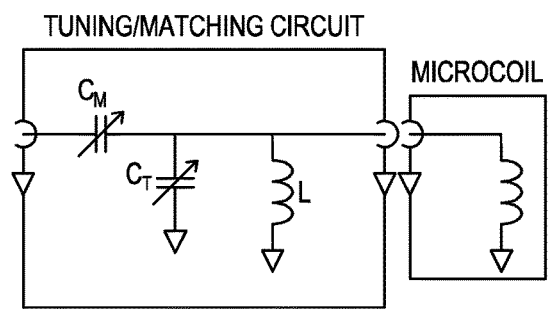

Two tuning circuits were constructed for use in the Example as shown in FIGS. 5A and 5B. In both cases, the microcoil was mounted by itself in a cast aluminum box, while the external tuning inductor L and tuning and matching capacitors $C_T$, $C_M$ were mounted in a separate aluminum box. The capacitors are adjusted to yield an input impedance of 50 Ohms for the combined circuit. In the first circuit (FIG. 5A), a quarter-wave ($\lambda/4$) (50 Ohm characteristic impedance) cable was used to transform the coil resistance to a higher value and then placed this transformed impedance in parallel with the tuning inductor. In this case, the full resonant voltage was applied to the (transformed) sample coil impedance. In the second circuit (FIG. 5B), the connection between the two parts of the circuit was short, and the sample coil and tuning inductor were in series, so that all of the resonant current flowed through the sample coil.

The two circuits exhibited nearly identical SNR performance. All subsequent measurements were performed with the first circuit (FIG. 5A), because the remote placement of the tuning and matching elements made it more convenient to work with. The external "tuning" inductor in this circuit was 5 turns of 14 gauge bare copper wire, with a calculated inductance of 0.25 µH, and a calculated resistance at 44.2 MHz of 0.07Ω. Hence, the tuning inductor contributes negligibly to resistive noise; the tuning circuit is therefore as efficient as a conventional circuit made without the extra tuning inductor. The tuning and matching capacitances were both approximately 22 pF. The large value of the matching capacitance resulted from the high losses in the microcoil. Because the Wavetek radio frequency sweeper used in the Example operates at the milliwatt level, and there was reluctance to subject the microcoil described above to this power, the Q of the resonant circuit was estimated by constructing a mockup of the microcoil using robust 36 gauge copper wire and a 5 Ω(ohm) resistor. The mockup circuit had a Q of about 10, as measured from the halfpower points on the sweeper output.

Figure 6:
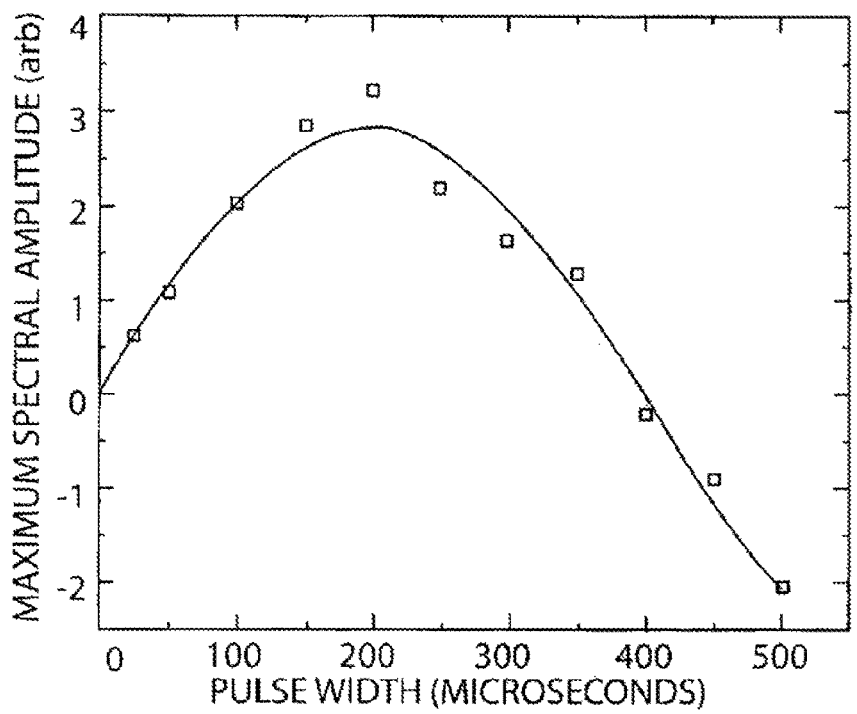
FIG. 6 shows determination of the Π-pulse width in the microcoil from a water sample. The spectral intensity is plotted as a function of excitation pulse width. Transmitter power was 0.25 mW. The line is a sine wave fit to the data wherein the Π-pulse length given by this fit is 397±4 µs (microsecond).

The nutation performance of the microcoil probe is shown in FIG. 6, where the signal intensity, after an excitation pulse, from a sample of de-ionized water, is plotted as a function of pulse width α. The data followed a typical sin(α) curve, indicating uniform sample excitation by a homogeneous RF field. The Π-pulse width, determined from fitting the sine curve, was 397±4 μs. The transmitter amplitude was 0.32 V (peak-to-peak), corresponding to a power into 50Ω of only 0.25 mW. A Π/2-pulse time of 200 μs corresponds to an RF field strength of 0.3 G, which is produced in the coil by a current of 1.8 mA.

Figure 7:
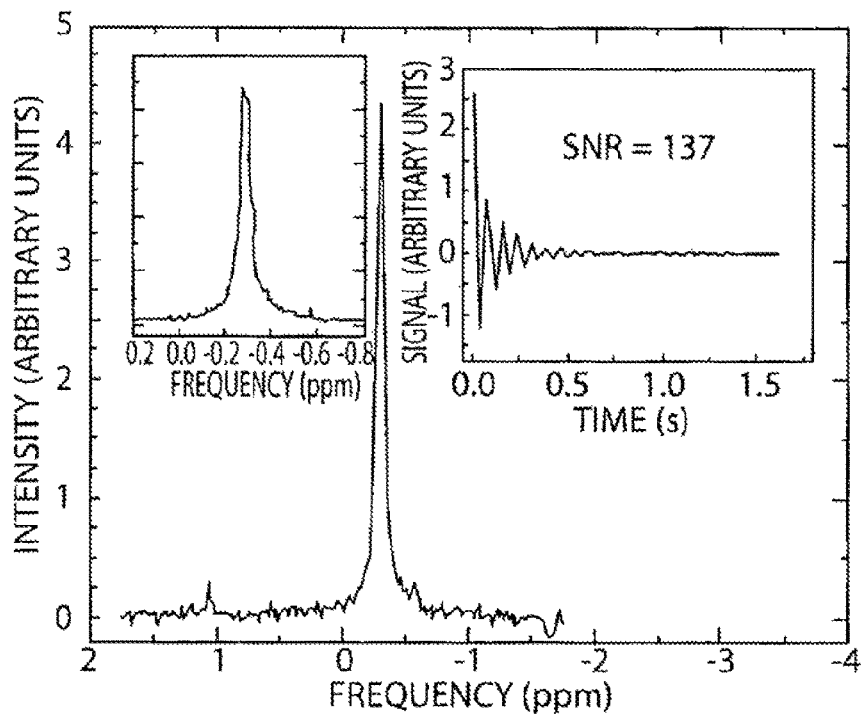
FIG. 7 shows an absorption spectrum of a sample of de-ionized water, calculated by Fourier-transforming the FID (free-induction decay) from a single Π/2 pulse of width 200 µs. The full width at half maximum is 2.5 Hz, and the line is nearly Lorentzian, as shown by the left inset. The right inset shows the FID. The time domain data were acquired at 200 µs per point and then digitally filtered to 6.4 ms per point (decimated by 32). The signal to noise ratio, measured as the initial FID amplitude divided by the standard deviation of the baseline noise, is 137. The small peaks near −1.7 and +1.1 ppm (marked by *) are 60 Hz sidebands of the main peak; they result from gain variations in the receiver used.
Figure 8:
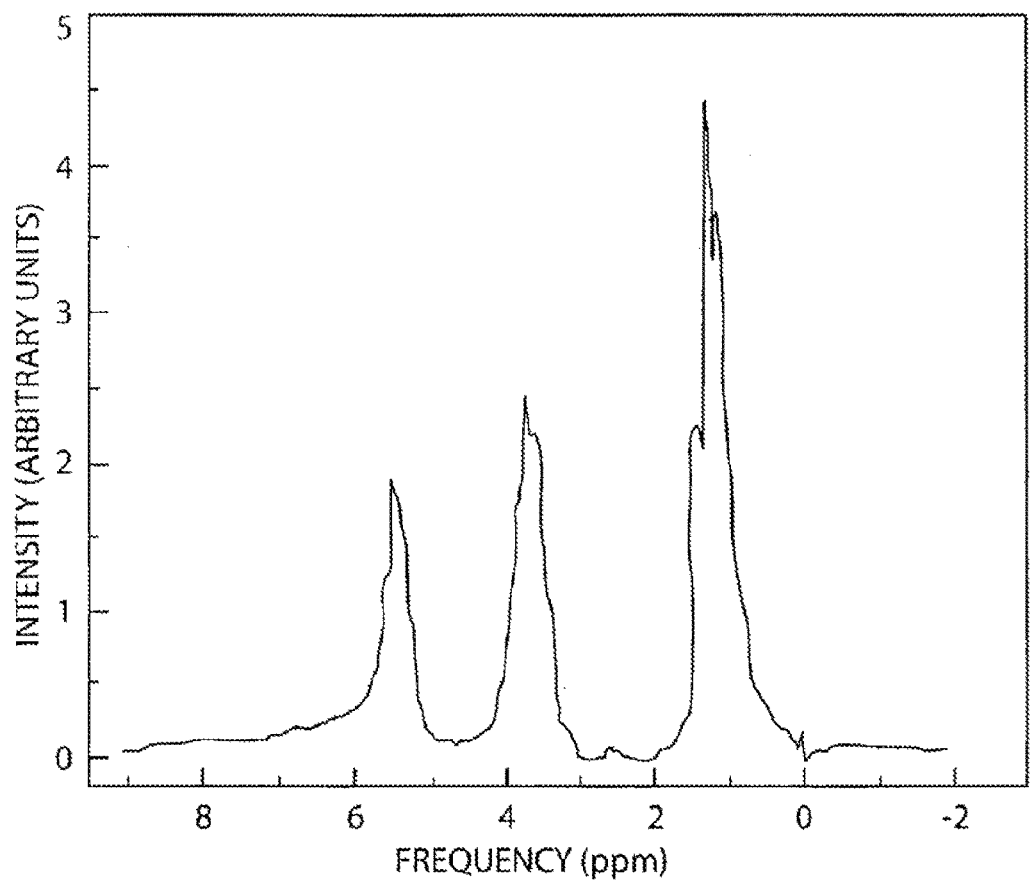
FIG. 8 is a spectrum of 100% ethanol taken with 64 FIDs, 8192 pts, 100 µs per point, 10 kHz filters (the lowest available), decimated by 4, with a 5 s (second) relaxation delay. The parameters for a fit of the spectrum to the sum of three Gaussians are listed in Table 1.

The free-induction decay (FID) and spectrum of deionized water in the microcoil are shown in FIG. 7. The spectrum has a full-width at half maximum (FWHM) of 2.5 Hz (0.056 ppm) and is reasonably well-fit by a Lorentzian, as shown in the left inset. (At 55% and 11% of maximum, the widths are 2.3 Hz and 8.7 Hz, respectively.) The SNR after a single Π/2 pulse was found to be 137 (ratio of FID amplitude to rms baseline noise). The small sidebands at ±60 Hz were presumably due to gain modulations in the receiver amplifiers used, caused by 60 Hz ripple. (Sidebands ±120 Hz were also observed.) FIG. 8 shows the NMR spectrum of a sample of 100% ethanol, calculated from 64 FIDs acquired with a 5 s repetition time. Peaks are seen at δ=1.2, 3.7, and 5.5 ppm, corresponding to the $CH_3$—, $CH_2$—, and —OH protons, respectively, with the correct relative amplitudes of 3:2:1 (Table 1). Note also the observation of the approximate 7 Hz J-coupling for the methyl group, and the smaller couplings for the methylene and hydroxyl protons, indicating that the frequency drift over the 5-minute experiment was less than 3 Hz. For both the water and the ethanol experiments, only the X, Y, and Z gradients were shimmed because higher order shims were not available.

TABLE 1

Fit of the ethanol spectrum to the sum of three Gaussians

| δ(ppm) | Multiplicity | Amplittude | |
|---|---|---|---|
| 1.2 [1.2][a] | [3] | 3.0 | [3] |
| 3.70 [3.65] | [4] | 1.9 | [2] |
| 5.48 [5.275] | [1] | 1.1 | [1] |

[a] The standard values are shown in square brackets

Figure 9A:
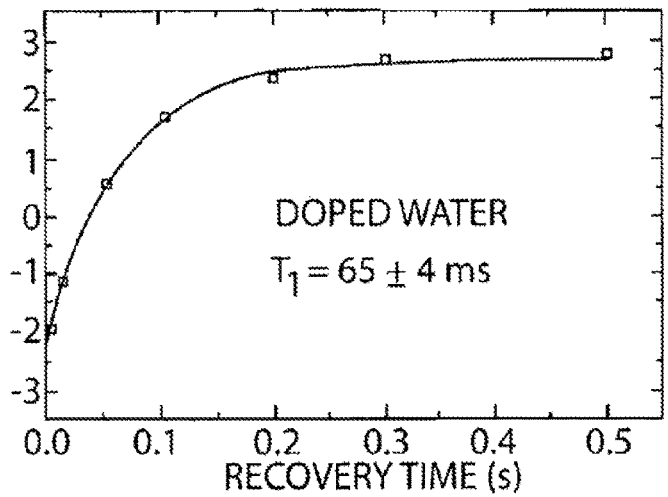
FIGS. 9A, 9B, and 9C show measurement of the longitudinal relaxation times for three samples of water in the microcoil.
Figure 9B:
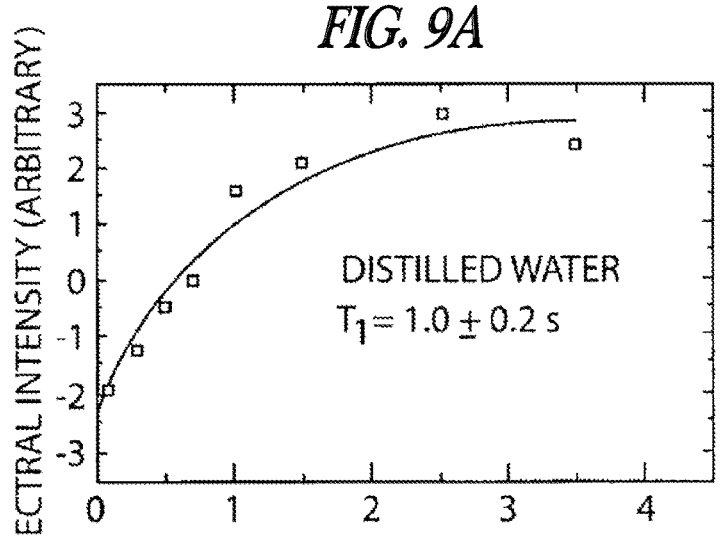
Figure 9C:
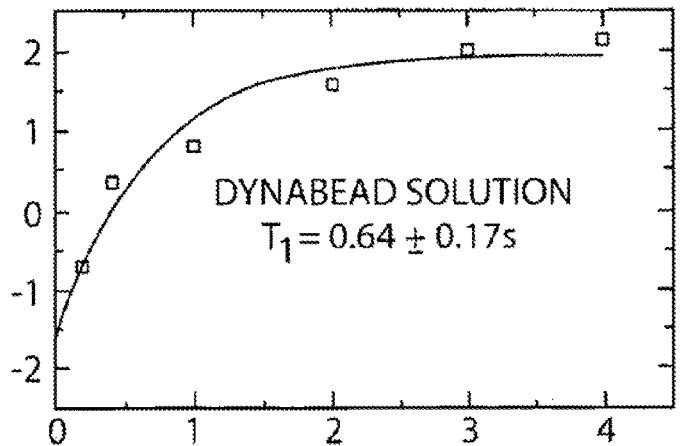

To test the ability of the microcoil to measure spin-lattice relaxation times, three different water samples were used; the first sample was doped with Gd-DTPA to shorten the $T_1$ to around 70 ms, the second sample consisted of pure de-ionized water, and the third sample contained magnetic beads (at a concentration of 1000 beads/nL) in de-ionized water. In all cases, a single scan was acquired at each recovery time. The results (FIG. 9A, 9B, 9C) show that relaxation times can be accurately measured for both shorter (65 ms) and longer (0.6 and 1.0 s) $T_1$ values with a standard inversion-recovery pulse sequence. The 397 μs Π-pulse gave clean inversion of the magnetization for all samples.

Figure 10:
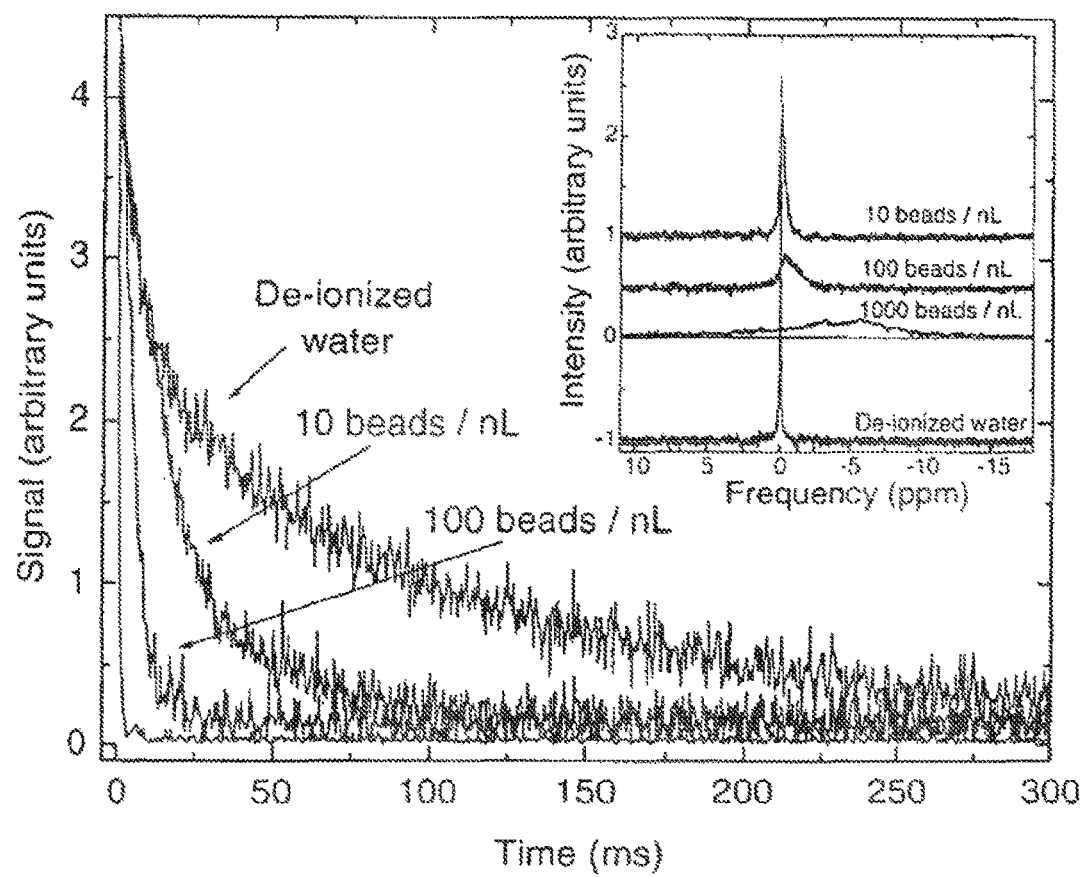
FIG. 10 shows effect of SPIONs (Dynabeads) on the transverse ($T_2^*$) relaxation time of water in the microcoil. The first 300 ms of the free induction decays for the de-ionized water sample, as well as water samples containing 10, 100, and 1000 beads/nL (not labeled), are shown. For the first three samples, a single scan, digitally filtered to an effective acquisition rate of 400 µs per point, is shown. For the 1000 beads/nL sample, 16 scans were averaged together. The inset shows the $^1H$ NMR spectra from the FIDs, showing both the increase in line width and the shift to lower frequency due to the presence of the magnetic beads.

In FIG. 10, the signal detected from deionized water and three different dilutions of the stock Dynabead solution, corresponding to 1000, 100, and 10 beads/nL are compared. The magnitude of each FID is shown, so that they all appear as if they were on resonance. The data are acquired after a single Π/2 pulse, digitizing at 100 μs per point (200 μs per point for the deionized water). The data were digitally filtered to achieve an effective digitization time of 400 μs per point. For the 1000 beads/nL sample, 16 FIDs were averaged together; the other data are each a single FID. The beads have two effects on the water spectral peak: the peak broadens and shifts to lower frequencies as the concentration of beads increases. The reduction in $T^*_2$ is apparent in the FIDs. The inset of FIG. 10 compares the spectra of the four solutions and shows both the linebroadening and the shift to lower frequency caused by the beads. Data for a 1 bead/nL sample (not shown) were indistinguishable from the deionized water data.

Figure 11A:
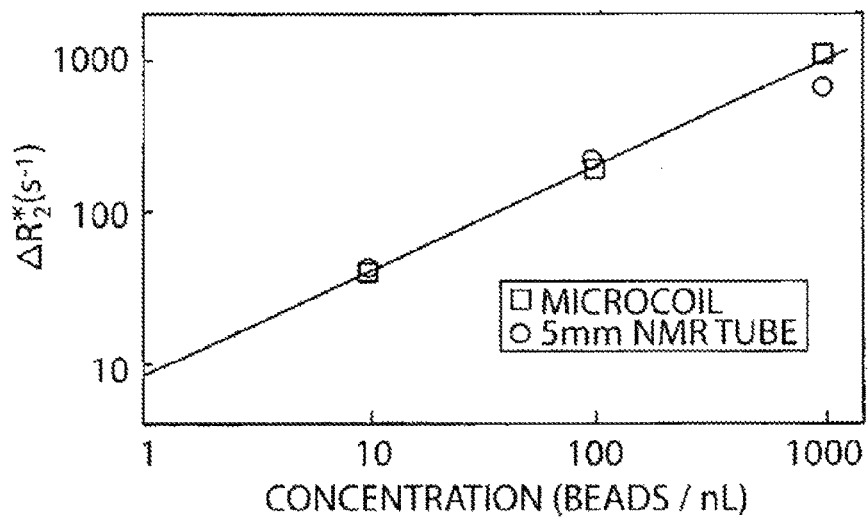
FIG. 11A shows change in $1/T_2^*$ due to the presence of 1 µm magnetic beads as a function of concentration. The solid squares are data obtained using a 264 nL microcoil, while the open circles are data obtained from the same bead solutions in 5 mm NMR tubes using a conventional probe. The straight line, drawn as a guide to the eye, has a slope of roughly ⅔ on this log-log plot, indicating that $\Delta R_2^*$ is proportional to the ⅔ power of concentration over this range.
Figure 11B:
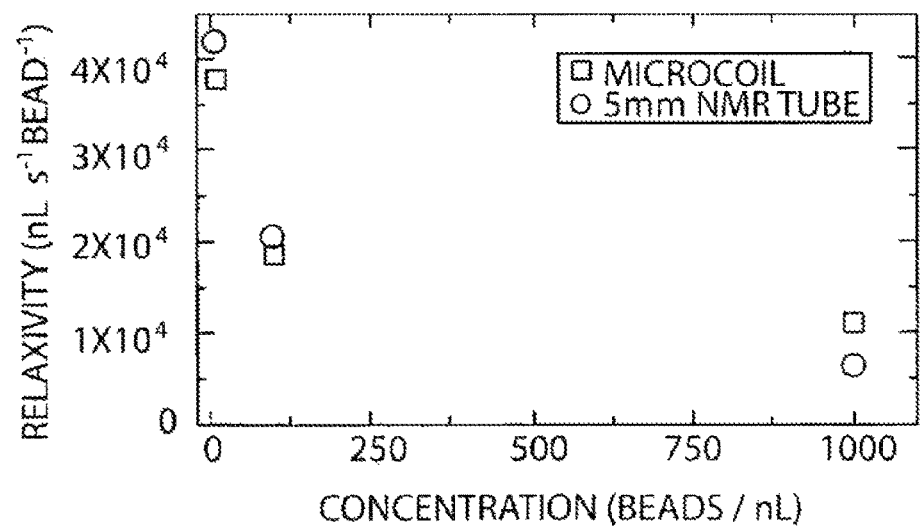
FIG. 11B shows relaxivity $r_2^*$ of the magnetic beads as a function of concentration. Per bead, the enhancement of $1/T_2^*$ increases with decreasing concentration.

The solid symbols in FIG. 11A give the observed change in $1/T^*_2$ ($\Delta R^*_2$) due to the presence of the beads, as a function of bead concentration, C. Here, $\Delta R^*_2 = R^*_{2\ bead\ solution} - R^*_{2\ water}$ and $R^*_2 = \Pi\Delta f$, where $\Delta f$ is the FWHM in Hz of the Lorentzian line fit to each spectrum in FIG. 10. Note that both axes in FIG. 11A are logarithmic; the straight line (drawn as a guide to the eye) has a slope of roughly ⅔ indicating that $\Delta R^*_2$ is proportional to $C^{2/3}$ over this range of bead concentrations. The relaxivity $r^*_2 (= \Delta R^*_2/C)$ is therefore not a constant, but decreases with increasing concentration as shown in FIG. 11B.

Because magnetic field gradients can cause motion of the magnetic beads with respect to the fluid, it was not clear a priori that the concentration of beads delivered to the microcoil would be the same as the concentration in the supply syringe. Indeed, the measured $T^*_2$ of bead solutions in the microcoil was observed to decrease over time if the bead solution was allowed to sit motionless in the coil over several minutes, suggesting that the spatial distribution of the beads was changing, due to clustering, settling, or migration out of the coil. Thus, in order to validate the microcoil results, the $T^*_2$ of the same bead solutions (1000, 100, and 10 beads/nL) and deionized water in capped 5 mm NMR tubes using a conventional probe in the same magnet. Each measurement was performed within 20-30 s after shaking the tube to homogenize the bead solution, and the tube was immediately extracted afterwards to visually confirm that the beads had not settled during the measurement. (Shimming was performed on the deionized water, and a sample holder was used to position the other 5 mm tubes identically, to avoid the need to re-shim. Repeatedly placing the same sample in the probe using this holder gave linewidths that were reproducible to ±5 Hz.) Migration of the beads was similarly observed in the 5 mm tubes (both visually and as an increase in $T^*_2$ over time) if the samples were allowed to sit in the magnet for longer time periods. The $\Delta R^*_2$ values measured for the bead solutions in 5 mm tubes (open symbols in FIG. 11A) are in good agreement with those obtained for the same concentrations in the microcoil, indicating that the expected concentrations were delivered to the microcoil.

Thus, in summary, the nutation performance of the microcoil was sufficiently good so that the effects of magnetic beads on the relaxation characteristics of the surrounding water could be accurately measured. The solution of magnetic beads (Dynabeads MyOne Streptavidin) in deionized water at a concentration of 1000 beads per nL lowered the $T_1$ from 1.0 to 0.64 s and the $T^*_2$ from 110 to 0.91 ms. Lower concentrations (100 and 10 beads/nL) also resulted in measurable reductions in $T^*_2$, indicating that low-field, microcoil NMR detection using permanent magnets can be used as a high-sensitivity, miniaturizable detection mechanism for very low concentrations of magnetic beads in biological fluids.

The tuning circuit described above is capable of tuning an arbitrarily small inductance at a frequency compatible with a permanent magnet, coupled with the 550 μm microcoil, allows spectroscopic and relaxation measurements using less than 1 mW of radiofrequency power. (This low power requirement further aids in making the NMR detector portable.) The line widths for deionized water are adequate for the detection of magnetic beads in water at a concentration of 10 beads/nL. The coil used for these proof-of-principle measurements is not optimized in size for NMR sensitivity, as discussed further below. However, the above results indicate that this approach will allow the detection of very dilute biological species, perhaps as rare as a single cell or molecule labeled with a single magnetic bead.

The challenge of achieving this detection sensitivity can be discussed quantitatively in light of the data of FIGS. 10 and 11. In a portable detector system pursuant to the invention, a fluid containing very dilute, magnetically labeled biological objects flows through a approximate 1 nL volume coil while the FID is monitored. The challenge is to detect the difference between the FID of the background fluid and the same fluid containing one magnetic bead (nanoparticle) within the coil volume. Considering FIG. 10, the change in $T^*_2$ of water can be readily detected due to 10 beads/nL, or roughly 3000 magnetic beads (nanoparticles) in the Example microcoil (264 nL volume). Achievement of a similar $T^*_2$ for deionized water (approximate 100 ms) and adequate SNR in a microcoil with a 1 nL sample volume permits detection of 10 beads (nanoparticles).

Extrapolating the straight line in FIG. 11A indicates that the $\Delta R^*_2$ of one bead in a 1 nL volume is about 8 s$^{-1}$, which would have caused an increase in the linewidth of water in the Example microcoil from about 3 to about 6 Hz. This increase should have been detectable given the high SNR. That such a change in line width due to the 1 bead/nL solution was not detected suggests that the $\Delta R^*_2$ for this concentration is lower than that predicted by extrapolating the straight line in FIG. 11A. A theoretical treatment of dipolar broadening of the NMR line due to dilute magnetic impurities indicates that the linewidth will be proportional to $C^{1/2}$ at higher concentrations and will be linear in C at lower concentrations. The above slope of ⅔ suggests that the example conditions are in the transition region between these two limits such that a higher slope at lower concentration should be expected, resulting in a predicted value of $\Delta R^*_2$ lower than 8 s$^{-1}$ at 1 bead/nL. Hence, the detection of a single 1-μm Dynabead in a 1 nL coil will require achievement of an even narrower line width, while at the same time detecting adequate signal strength.

A 100 μm diameter coil (1 nL) will give substantially less signal than the Example 264 nL microcoil due to the reduced sample size. Thus one must consider whether such a coil will have sufficient SNR to detect 10 beads in its 1 nL volume. In the "large" microcoil data in FIG. 10, detection sensitivity can be maximized by integrating the FIDs, say from 50 to 300 ms, which is roughly equivalent to applying strong digital filtering. These integral values are 397 and 122 (arbitrary units), for the water and 10 beads/nL data, respectively. The uncertainty in these values is 3, which corresponds to a signal to noise ratio (SNR) of 133 for determining the amplitude of the water signal. The smaller 1 nL volume coil will have much less signal, but also less noise (due to its lower resistance). For microcoils in the limit where skin depth is small compared to wire size (which is not quite true for our coil), the SNR per unit volume scales as the inverse of the coil diameter. Hence, the absolute SNR scales as the square of the linear dimension of the sample. The invention envisions scaling the sample and coil dimension down by roughly a factor of 6, so that the SNR in the determination of the integrated water signal amplitude will be about 3.7. Hence, the 1 nL coil will require that the beads (nanoparticles) change the area under the FID of the background water by at least 25%. In this Example, a concentration of 10 bead/nL caused a 70% change in the integrated signal from 50 to 300 ms, and therefore may remain detectable in the 1 nL coil, provided that a similar background water $T^*_2$ is achieved.

While the Example microcoil described above is already capable of detecting the presence of as few as 3000 magnetic beads (nanoparticles), it can be further optimized for maximal SNR performance for operation at 44.2 MHz. The thickness of the coil "wire" is much less than a skin depth, which raises the resistance of the coil without providing any improvements in signal detection. The width of the "wire" is much more than a skin depth, so that it may be possible to increase the number of turns per unit length and gain in coil sensitivity without suffering a nullifying increase in resistance. Careful attention to the geometrical design of the smaller microcoil, should improve the SNR above the estimate of about 3.7 based on this Example. SNR performance will be enhanced by reducing the coil resistance, which is higher than expected in Example ion-milled microcoil. Improving the line width of the background fluid places a lower demand on the SNR performance. The use of susceptibility matching (either in the choice of evaporated metals or via a matching fluid) and the reduction of the filling factor (by increasing the relative wall thickness in the capillary tube) may improve the line widths in smaller coils. In addition, the permanent magnet used in the Example is not very homogeneous and only first order shims are available; a more homogeneous applied field may be required to achieve narrower lines. Optimization of the coil can also include comparisons of both the SNR and line width performance of ion-milled coils to other types of microcoils, such as copper wire-wound coils. Some compromise between line width and sensitivity may provide the best opportunity for detecting single biological objects.

The surface of a single cancer cell (about 10 μm in diameter) can bear upwards of $10^5$ binding sites (antigens) for a particular antibody and can accommodate up to 400 one micron diameter magnetic beads (nanoparticles), assuming monolayer coverage and random close packing. Thus, sensitivity to 10 beads would already be adequate to detect single magnetically labeled cells. On the other hand, bacterial toxin molecules (e.g., botulism toxin) are much smaller and would accommodate only one or a few beads, requiring single-bead detection sensitivity. Hence, single-bead sensitivity is envisioned by practice of the present invention.

So far in the Example, the detection limits have been based on measurements of a particular type (Dynabeads) and size (1 μm) of magnetic bead (nanoparticle). Larger magnetic beads (having larger magnetic moments) are available and will permit an increase in the relaxivity of a single bead and further lower the detection limit. Assuming that a background $T^*_2$ was at least 100 ms, the $\Delta R^*_2$ for a single 1.63 μm bead in a 1 nL volume to be at least 60 s$^{-1}$, which should be readily detected using a 1 nL microcoil with a background water $T^1_2$ of 100 ms and a SNR of about 3. Even larger beads (e.g., 2.8-μm and 4.8-μm Dynabeads) are commercially available, and may be used, if necessary, to further enhance the ability to detect a single magnetic bead in an NMR microcoil.

Although the invention has been described hereinabove in terms of specific embodiments thereof, it is not intended to be limited thereto but rather only to the extent set forth hereafter in the appended claims.

What is claimed is:

1. A method for detecting a target analyte in a sample, the method comprising:
   introducing magnetic particles comprising target-specific moieties to a sample comprising a plurality of target analytes under conditions such that at least one cluster of magnetic particles and target analytes is formed; and using a nuclear magnetic resonance (NMR) device in order to measure a signal due to a change in relaxation rate, wherein the relaxation rate changes in the presence of the at least one cluster, thereby detecting the target analyte in the sample.

2. The method according to claim 1, wherein measuring is accomplished in the presence of other components in the sample.

3. The method of claim 1, wherein the changes are selected from relaxation times T1, T2, T2*, or a combination thereof.

4. The method according to claim 1, wherein the NMR devices comprises:
   a magnet configured to produce a magnetic field;
   a vessel configured to hold the sample and being located within the magnetic field;
   a radio frequency (RF) coil located within the magnetic field.

5. The method according to claim 4, wherein the RF coil wraps around the vessel.

6. The method according to claim 4, wherein the magnetic is a permanent magnet.

7. The method according to claim 1, wherein the target-specific moieties are antibodies.

8. The method according to claim 1, wherein the sample is a biological sample.

9. The method according to claim 8, wherein the biological sample is blood or urine.

10. The method according to claim 1, wherein the magnetic particles are superparamagnetic particles.

\* \* \* \* \*